US005725594A

United States Patent [19]

McTighe et al.

[11] Patent Number: 5,725,594
[45] Date of Patent: Mar. 10, 1998

[54] PROXIMAL CONICAL STEM

[75] Inventors: Timothy McTighe, Chagrin Falls, Ohio; Jerry Kee, Salt Lake City, Utah; Paul Mraz, Chagrin Falls, Ohio

[73] Assignee: Ortho Development Corporation, Draper, Utah

[21] Appl. No.: 600,118

[22] Filed: Feb. 12, 1996

Related U.S. Application Data

[63] Continuation of Ser. No. 274,956, Jul. 14, 1994, abandoned.
[51] Int. Cl.$^6$ .......................................................... A61F 2/34
[52] U.S. Cl. ................................................................. 623/23
[58] Field of Search ................................... 623/16, 18, 20, 623/19, 22, 23

[56] References Cited

U.S. PATENT DOCUMENTS

| Re. 28,895 | 7/1976 | Noiles . |
| 2,719,522 | 10/1955 | Hudack ................................... 623/23 |
| 3,605,123 | 9/1971 | Hahn . |
| 3,782,372 | 1/1974 | Smythe . |
| 3,782,373 | 1/1974 | Smythe ................................... 623/23 |
| 3,808,606 | 5/1974 | Tronzo . |
| 3,840,904 | 10/1974 | Tronzo . |
| 3,848,272 | 11/1974 | Noiles . |
| 3,894,297 | 7/1975 | Mittelmeier et al. . |
| 3,943,576 | 3/1976 | Silvash . |
| 4,031,571 | 6/1977 | Heimke et al. . |
| 4,068,324 | 1/1978 | Townley et al. . |
| 4,206,516 | 6/1980 | Pilliar . |
| 4,304,011 | 12/1981 | Whelan, III . |
| 4,352,212 | 10/1982 | Greene et al. . |
| 4,514,865 | 5/1985 | Harris . |
| 4,530,114 | 7/1985 | Tepic . |
| 4,549,319 | 10/1985 | Meyer . |
| 4,619,659 | 10/1986 | Witzel . |
| 4,670,015 | 6/1987 | Freeman . |
| 4,718,916 | 1/1988 | Morscher . |

(List continued on next page.)

FOREIGN PATENT DOCUMENTS

| 549 | 7/1978 | European Pat. Off. . |
| 2472374 | 7/1981 | France ................................... 623/23 |
| 2651674 | 3/1991 | France ................................... 623/22 |
| 28 39 661 | 9/1979 | Germany . |
| 3125657 | 1/1983 | Germany ................................... 623/23 |

(List continued on next page.)

OTHER PUBLICATIONS

Freeman et al., in The Young Patient with Degenerative Hip Disease, Sevastik J. Goldie I (ed.), Stockholm, Sweden, 1986, pp. 281–292.

Cook et al., Journal of Biomedical Materials Research, 18, 497–512, (1984).

Yue et al., Journal of Biomedical Materials Research, 18, 1043–1058, (1984).

Zimmer "Implant Metals" product catalog Rev.2A, (Sep. 1974).

"The Freeman Total Hip System," Corin Medical Limited, Gloucestershire, England, 1985.

Freeman, M.A.R., "Why Resect the Neck?", The Journal of Bone and Joint Surgery, vol. 68–B, No. 3, May 1986, pp. 346–349.

(List continued on next page.)

*Primary Examiner*—David Isabella
*Attorney, Agent, or Firm*—Thorpe, North, Western, L.L.P.

[57] ABSTRACT

A cementless femoral hip stem component includes an elongate stem having opposing distal and proximal sections. The proximal section includes a conical stem surface which terminates in a proximal end. A collar having a conical undersurface extends laterally outward from the proximal end of the stem. The proximal conical stem portion and the conical undersurface of the collar cooperatively define a unitary double-cone contact surface to allow the collar to subsidably engage with external cortical bone in tandem with the proximal conical stem subsidably engaging with the internal femoral canal.

23 Claims, 2 Drawing Sheets

U.S. PATENT DOCUMENTS 4,888,023  12/1989  Averill et al. .
4,944,762  7/1990  Link et al. .
5,062,854  11/1991  Noble et al. .
5,314,489  5/1994  Hoffman et al. .

FOREIGN PATENT DOCUMENTS 426096  6/1967  Switzerland ............................. 623/22
83/02555  8/1983  WIPO .
WO85/03426  8/1985  WIPO .

OTHER PUBLICATIONS

"In Vitro Study of Initial Stability of a Conical Collared Femoral Component", Fischer, Carter and Maloney, The Journal of Arthroplasty vol. 7 Supplement 1992.

"Horizontal Platform–Supported Total Hip System HPS II Achieving Physiological Stress Distribution with a Versatile Porous–Coated or Smooth–Stemmed System", Designed by Charles O. Townley, M.D., Depuy 1986.

"New Jersey LCS Hip System", Depuy 1991.

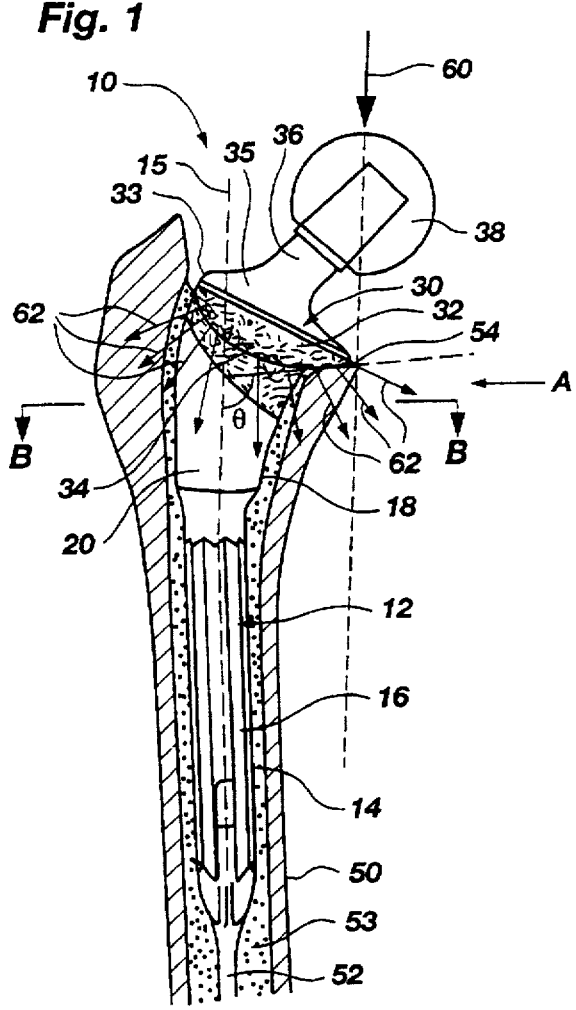
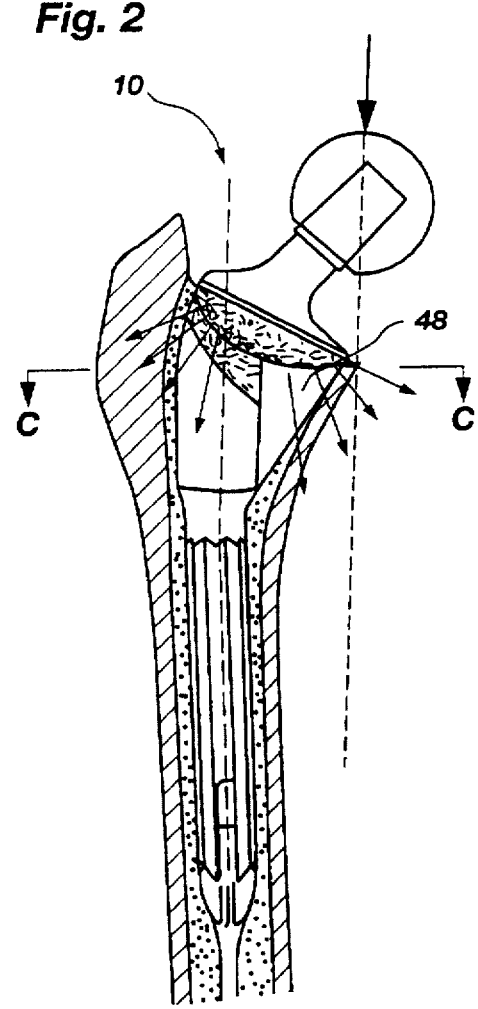
Fig. 1
Fig. 2
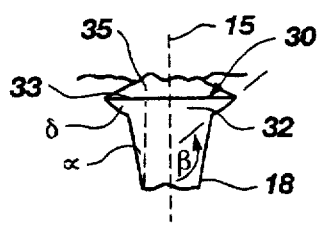
Fig. 1A
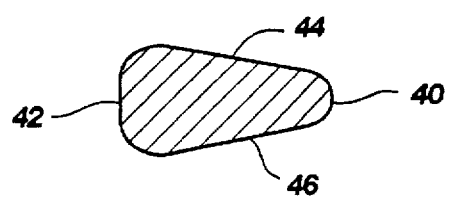
Fig. 1B
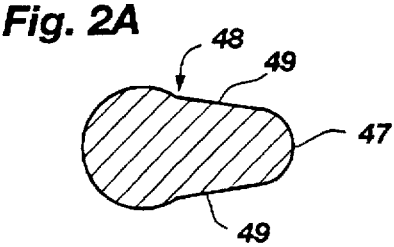
Fig. 2A
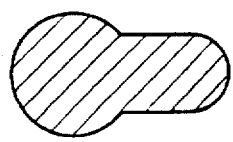
Fig. 3
(PRIOR ART)

PROXIMAL CONICAL STEM

This application is a continuation of U.S. application Ser. No. 08/274,956, filed Jul. 14, 1994, now abandoned.

BACKGROUND OF THE INVENTION

1. The Field of the Invention

The present invention relates generally to the field of artificial joints. More particularly, it concerns a femoral component of a cementless hip stem prosthesis which provides a unitary double-flared contact surface for subsidable engagement with interior and exterior portions of the femur.

2. The Background Art

It is known in the art to replace the hip joint with an artificial hip stem replacement. Numerous artificial implants are available which can be installed to replace the natural hip joint with an artificial ball and socket combination. A passage called the medullary canal is reamed or bored in the upper end of the femur. A stem or femoral component of an artificial implant is inserted into the reamed portion of the medullary canal in a secure, seated position. A neck member extends outward and away from the stem and terminates in a spherical knob for insertion into the acetabulum of the hip in rotational contact therewith about the three major orthoganal axes.

A hip prosthesis generally includes a collar or support plate disposed upon a proximal portion of the stem. The under surface of the support plate in most hip prostheses is flat and is disposed at an angle to the major direction of load, as shown for example in U.S. Pat. Nos. 5,314,489 (issued on May 24, 1994 to Hoffman et al.) and 4,888,023 (issued on Dec. 19, 1989 to Averill et al.). The planer geometry and angular orientation of prior art collars offer only limited capacity for force transfer. Prevailing hip stem philosophy dictates that the proximal portion of the stem provide the bulk of the force transfer, with the collar providing only minimal bone contact simply to prevent the stem from sinking too deeply into the femur. The thinking is that if the collar becomes fully seated it could prevent the proximal stem portion from fully engaging, resulting in less stress being transferred to the prosthesis/bone interface. Thus, prior art collars are designed to be flat and are configured so as to avoid fully-seated contact with the cortical bone.

The prior art femoral components are characterized by a number of disadvantages. The major load is transferred radially outward from the proximal stem portion in tension, or "hoop stress" as it is referred to in the art. However, the femur is designed to accept loads from the hip joint in compression and not tension, and the tensile hoop stresses cause thigh pain in the patient. Further, the primary radial contact is less stable and allows for micromotion of the stem, making it difficult for the stem to achieve a position of stability. The micromotion decreases vital bone growth at the contact interface, further inhibiting stabilization. The planer geometry of the collar fails to permit settling of the collar in tandem with settling of the proximal stem portion which further inhibits stabilization. The flat collar actually tends to block settling. The prior art also fails to adequately inhibit osteolysis caused by wear debris introduced into the femoral canal at the site of the collar.

Relatively recent attempts to improve the state of the art include U.S. Pat. No. 4,944,762 (issued on Jul. 31, 1990 to Link et al.), which represents an attempt to improve the transfer of forces between the under surface of collar and the resection surface of the femur. However, such attempts are actually designed to prevent settling, as tacity admitted in the Link et al. patent in col. 2 at lines 1–5. Link et al. explains therein that the resection surface should be meticulously shaped to enable secure interlocking with the under surface. However, a secure interlock between the under surface of the collar and the resection surface prevents the prosthesis from settling to a position of stability. The Link et al. patent thus solves one problem but introduces others.

OBJECTS AND SUMMARY OF THE INVENTION

It is therefore an object of the present invention to provide a proximal prosthetic component for use in the replacement of joints.

It is another object of the invention to provide such a prosthetic component which replaces hoop stress with increased compressive force.

It is a further object of the invention to provide such a prosthetic component which is simple in design and manufacture.

It is an additional object of the invention to provide such a prosthetic component which enables increased surface area of contact with bone and corresponding reduction in the occurrence of gaps at the bone/prosthesis interface.

It is still another object of the invention to provide such a prosthetic component which reduces micromotion and thereby increases bone growth stimulation.

It is yet another object of the invention to provide such a prosthetic component which inhibits introduction of wear debris into the femoral canal.

The above objects and others not specifically recited are realized in a specific illustrative embodiment of a femoral hip stem component. An elongate stem includes opposing distal and proximal sections. The proximal section includes a conical stem surface which terminates in a proximal end. A collar having a conical undersurface extends laterally outward from the proximal end of the stem. The proximal conical stem portion and the conical undersurface of the collar cooperatively define a unitary double-cone contact surface to allow the collar to subsidably engage with external cortical bone in tandem with the proximal conical stem subsidably engaging with the internal femoral canal.

Additional objects and advantages of the invention will be set forth in the description which follows, and in part will be apparent from the description, or may be learned by the practice of the invention. The objects and advantages of the invention may be realized and obtained by means of the instruments and combinations particularly pointed out in the appended claims.

BRIEF DESCRIPTION OF THE DRAWINGS

The above and other objects, features and advantages of the invention will become apparent from a consideration of the subsequent detailed description presented in connection with the accompanying drawings in which:

FIG. 1 illustrates a side view of a hip prosthesis made in accordance with the principles of the present invention;

FIG. 1A illustrates a fragmented front view of the hip prosthesis of FIG. 1;

FIG. 1B illustrates a cross sectional view of a proximal portion of the hip prosthesis of FIG. 1, taken along section B—B FIG. 2 illustrates a side view of an alternative embodiment of the hip prosthesis of FIG. 1;

FIG. 2A illustrates a cross sectional view of a proximal portion of the hip prosthesis of FIG. 2, taken along section C—C;

FIG. 3 illustrates a cross sectional view of prior art hip stem geometry;

DETAILED DESCRIPTION OF PRESENTLY PREFERRED EMBODIMENTS

Figure 4:
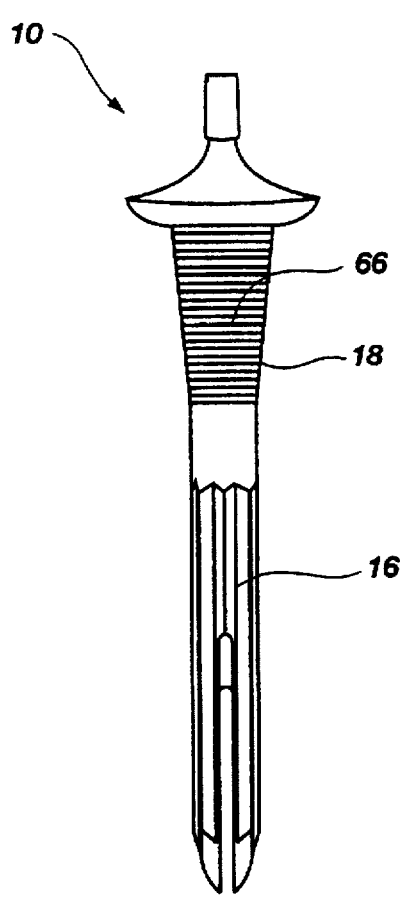
FIG. 4 illustrates a front view of an alterative embodiment of the hip prosthesis of FIG. 1.

Referring now to FIG. 1, there is shown a prosthesis generally designated at 10. The prosthesis 10 includes an elongate stem 12 and a collar or support plate 30 attached thereto. The stem 12 includes a fluted distal section 14 and an opposing proximal section 18, centered generally around a long axis 15 of the stem. The distal section 14 has a plurality of longitudinal flutes 16 formed therein, and the proximal section 18 includes a proximal exterior surface 20 defining a conical contact surface. The term "distal" as used herein refers to the portion of the prosthesis 10 positioned farthest within a femoral canal 52 of a femur 50.

The collar, designated generally at 30, includes a tapered under surface 32. The taper on under surface 32 preferably forms a circumferential frusto-conical surface in either symmetrical or asymmetrical fashion, but may be configured as any non-planar, generally tapering surface. The proximal surface 20 of the stem meets at a proximal edge thereof with the under surface 32 of the collar to form a circumferential transition section 34. The transition section 34 is preferably rounded so as to be characterized by an absence of corners and points, but may be alternatively defined by a corner. The proximal surface 20 of the stem and the under surface 32 of the collar both flare outwardly in a distal to proximal direction. These surfaces 20 and 32 may alternatively define any curvilinear or other nonplaner shape representing an average surface contour which flares outwardly in a distal to proximal direction. The collar 30 further includes a top side 35 configured to support a neck 36 having a hip ball 38 or other joint motion surface attached thereto.

It is preferred that the under surface 32 be flared at a greater degree of flare than the proximal surface 20 so as to form an angle therewith of less than 180 degrees. Referring now to FIG. 1A, there is shown a fragmented front view of part of the proximal section 18 and the collar 30 of FIG. 1 from the perspective of the direction shown by arrow A. The under surface 32 forms an angle $\delta$ with respect to a plane 33 inclined at an angle with respect to the long axis 15. The angle $\delta$ is preferably within a range of approximately twenty five to thirty five degrees, and most preferably thirty degrees. The top surface 35 may itself form the plane 33. The proximal surface 20 is flared at an angle $\alpha$, which is preferably about five degrees. Accordingly, the angle $\alpha$ shown in FIG. 1A causes the proximal section 18 to constitute a somewhat conical stem surface, and the angle $\delta$ causes the under surface 32 to constitute a somewhat conical plate surface, as shown in FIG. 1A.

Referring now to FIG. 1B, there is shown a cross sectional view of the proximal section 18, taken along section B—B. The proximal section 18 includes a medial side 40, lateral side 42, anterior side 46 and posterior side 44, corresponding to the medial, lateral, anterior and posterior directions as known in the medical art. Although it is preferred that the entire proximal surface 20 be flared, flaring may alternatively be confined to certain parts thereof such as to the anterior and posterior sides 46 and 44. In addition, flaring of the under surface 32 of the collar 30 may be alternatively confined to certain parts thereof, such as to the medial, anterior and posterior sides.

An alternative embodiment of the prosthesis 10 is shown in FIG. 2. Representative reference numerals provided in FIG. 1 should be read to apply also to FIG. 2. A medial triangular projection 48 is disposed to form the medial portion of the proximal section 18. The medial triangular projection 48 includes a rounded medial end 47 as shown in FIG. 2A. The rounded medial end 49 intercouples opposing sides 49 which flare outwardly from the medial end in medial to lateral directions. It can thus be seen by inspection of FIG. 2A that a cross section of the medial triangular projection 48 taken along horizontal plane section C—C, which is perpendicular to the long axis 15 of the stem 12, defines a conical section having a rounded tip.

The prosthesis is particularly adapted for use as a hip stem prosthesis. In use, the distal section 14 of the stem 12 is inserted in the medullary canal 52 of the femur 50. The femur 50 has been reamed and otherwise prepared beforehand in a manner known to those skilled in the art. The stem 12 is pressed into the canal 52 until the under surface 32 comes to rest upon hard, load-bearing cortical bone 54 of a lesser trochanter of the femur 50. The hip ball 38 is placed upon the neck 36 and inserted into the acetabulum (not shown) of the hip so as to function as a joint motion surface. The proximal conical surface 20 subsidably engages against side walls of the hollow interior medullary canal 52. Similarly, the conical under surface 32 subsidably engages against the load-bearing cortical bone 54.

It is to be understood that the under surface 32 is specifically designed to contact a substantial amount of the hard cortical bone 54 but still allow for subsidence or settling of the prosthesis 10. A non-limiting example of this subsidability is to form portions of the under surface 32 such that they are maintained at an angle relative to the long axis 15 which is greater than ninety degrees. For example, a medial portion of the under surface 32 preferably resides at an angle $\theta$ relative to the long axis 15 which is greater than ninety degrees, as shown most clearly in FIG. 1. Anterior and posterior portions of the under surface 32 reside at an angle $\beta$ relative to the long axis 15, the angle $\beta$ also being preferably greater than ninety degrees.

The angled relationships achieved by the flared geometry of the under surface 32 enable it to simultaneously accomplish two important functions: (i) transfer an increased amount of load 60 to the cortical bone 54 in compression, and (ii) subsidably engage with the cortical bone 54 so as to settle to a position of stability. The flared geometry of the proximal conical surface 20 also enhances subsidable contact. The overall effect is that the proximal conical surface 20 and the conical under surface 32 collectively form a unitary double-flared contact surface for maximum surface area of contact. Since both the proximal surface 20 and the under surface 32 are conical or otherwise flared, they provide increased surface area of contact with the femur 50 and permit settling of the prosthesis 10 to a position of stability. When the angles $\theta$ of FIG. 1 and/or $\beta$ of FIG. 1A are closer to ninety degrees, more of the load 60 is transferred to the femur 50 in the form of compression. The idea is to increase the amount of contact between the under surface 32 and the cortical bone 54, but in a subsidable manner.

It will be appreciated that the increased surface area of contact provided by the prosthesis 10, the settling capacity of both the proximal surface 20 and the under surface 32, and the corresponding stability provide a number of advantages over the prior art. Since the collar 32 is intended to contact the cortical bone 54 instead of avoid contact, the collar functions as a cap to substantially close off the upper portion of the femur 50. This capping action inhibits the introduction of osteolysis-causing wear debris into the medullary canal 52.

The increased proximal surface engagement of the cooperating conical surface 20 and under surface 32 is much more stable than the primarily tensile load transfer of prior art hip stems. Those skilled in the art will appreciate that the increased stability stimulates the bone for increased bone growth in accordance with Wolff's law, which provides that new bone growth is stimulated in direct proportion to the degree of loading upon the bone. The increased bone growth further enhances the stability of the prosthesis 10. Applicants have found that the increased stability operates to decrease micromotion of the prosthesis up to a factor of 10. In other words, where some prior art stems exhibit micromotion in certain areas of about 1000 microns, applicants' hip stem would respond with 100 microns of micromotion or less. When micromotion is substantially greater than 100 microns, the fibrous soft tissue interface between the inner medullary bone 53 and the prosthesis 10 is prevented from adhering to the prosthesis in new growth. This decreases stability and weakens the femur 50, and the present invention avoids such disadvantages because it loads the bone as much as possible in a stable manner for the other reasons discussed above.

The advantages discussed above can be present even if the circumferential transition section 34 defines a sharp corner. Desirable settling action of the prosthesis 10 can be enhanced by rounding the transition section 34 with a radius of curvature such that it is characterized by an absence of corners and points.

The prosthesis 10 is thus advantageously adapted for use as a cementless prosthesis. There is no question that bone cement has made and continues to make a significant contribution to the success of total hip replacements. However, it is important to recognize its inherent biological and mechanical limitations (low modulus, low fatigue strength, and toxicity). The present invention operates to transfer the load 60 into the femur 50 as compression, in accordance with the natural design of the hip joint and femur.

The present invention is also more user friendly. Too often the general orthopedist does not appreciate the required implantation technique for a given prosthesis design. Some tend to overextend indications. The lack of a full understanding of prosthesis design features and required surgical implantation techniques has led some surgeons to implant hip stem prosthesis incorrectly, in some cases predisposing the prosthesis to failure. It has been established that an important part of prior art hip stem prostheses is based on the concept of shaping the resection surface of the femur to correspond precisely to the under surface of the collar, so that the under surface interlocks securely with the resection surface (see U.S. Pat. No. 4,944,762 at col. 2, lines 1–5). This of course not only prevents the prosthesis from settling to a position of stability, it also requires precision cutting by the surgeon with little tolerance. However, since the present invention does not require interlocking but is specifically designed to enhance settling action, a less than perfect resection surface of the femur will not predispose the device to failure.

The medial triangular portion 48 of FIG. 2, although optional, offers a number of additional advantages, including additional surface area of contact. The increased surface contact provides increased rotational stability of the prosthesis 10. The medial to lateral flaring sides 49, shown in FIG. 2A, have been found by applicants to offer improved stability over the prior art "keyhole" geometry shown in FIG. 3.

Figure 5:
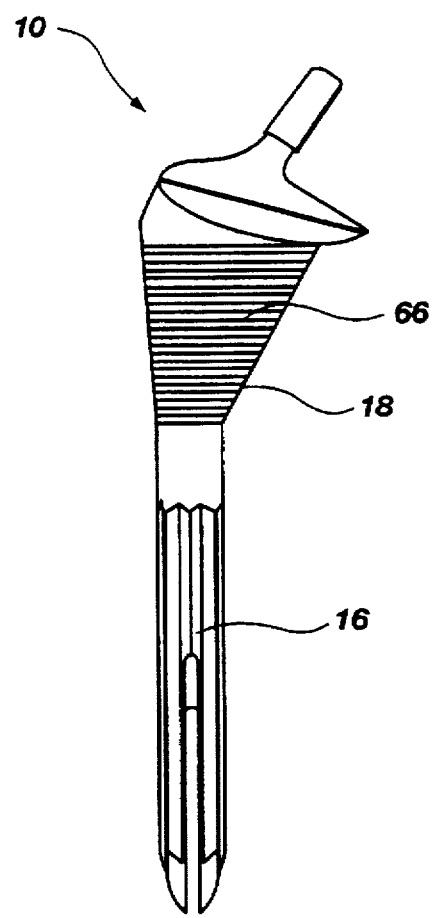
FIG. 5 illustrates a side view of the hip prosthesis of FIG. 4.

Referring now to FIGS. 4–5, it is to be understood that any embodiment of the prosthesis 10 may include circumferential terraces 66 formed in the proximal section 18. It will be appreciated that the terraces 66 are forced into engagement with the surrounding intra medullary bone 53 to block rotational movement of the prosthesis 10, and to stimulate supporting bone growth therearound. The longitudinal flutes 16 also operate to provide rotary stability to the prosthesis 10 relative to the femur 50.

The prosthesis 10 may be formed as a unibody device, or a modular device in the alternative. For example, the proximal section 18 could be a separable component from the rest of the stem 12, and the collar 30 could be a separable component from the proximal section 18. This alternative offers the advantage of selectively sizing two or more components to more precisely tailor the fit of the resulting total prosthesis to the specific internal contours of the patient.

A preferred method for replacing a joint in a patient in accordance with the principles of the present invention includes the steps of:

(a) selecting a prosthetic component including a flared proximal section and a flared plate section extending circumferentially outward from said flared proximal section such that said flared proximal and plate sections cooperatively form a unitary double-flared contact surface, and a joint motion surface extending outward from the plate section;

(b) inserting the prosthetic component into a medullary cavity of a first bone such that the flared proximal section subsidably engages with side walls of the medullary cavity in tandem with the flared plate section subsidably engaging with a load-bearing portion of the first bone such that the double-flared contact surface enables settling of the prosthetic component against contacting portions of the medullary cavity and load-bearing portion to a position of stability;

(c) inserting the joint motion surface into a second bone member to thereby enable load transfer between the first bone and the second bone member;

(d) preparing the load-bearing surface of the first bone and placing the flared plate section into contact therewith such that contacting portions of said flared plate section with the load-bearing surface form an angle with a long axis of the medullary cavity which is greater than ninety degrees to thereby enhance settling action of said flared plate section against said load-bearing surface.

The "flared plate section" referred to above as part of the preferred method refers to the under surface 32 shown in FIG. 1, which has been described herein as having "a greater degree of flare than the proximal surface 20." Thus, the medial section of the flared plate or under surface 32 extends outwardly from the proximal portion 18 of the stem 12 to define a type of overhang ledge relative to said proximal portion 18 as shown in FIG. 1. As also shown in FIG. 1, said overhang is greater than any overhang which might extend outwardly from a lateral portion of said proximal portion 18, the medial, lateral, anterior and posterior locations being decribed above in conjunction with FIG. 1B. As further shown in FIG. 1, there is preferably no overhang on the lateral side of the prosthesis 10.

It is to be understood that the phrase "greater than any overhang which might extend outwardly from a lateral portion of said proximal portion" as used herein shall refer broadly to lateral portions with overhangs as well as lateral portions without overhangs. The key is that the overhang defined by the flared plate or under surface 32 on the medial side is greater than any overhang extending outwardly from the lateral side, if any, this concept being supported by the overhang produced by the under surface 32 in FIG. 1. It is also shown in FIG. 1 that the under surface 32 forms an angle θ relative to the long axis 15 than resides somewhere within a range between ninety degrees and one hundred twenty degrees, and preferably less than one hundred degrees.

The present invention represents a significant advance in the field of artificial joint prostheses. It is to be understood that although the present invention has been illustrated herein in the context of hip joint replacement, it is equally applicable to any prosthetic application. For example, an embodiment of the present invention as described and claimed herein could be used to replace the knee joint. The disadvantages in the prior art noted above and others not discussed are overcome to a significant degree by the present invention. Those skilled in the art will appreciate from the preceding disclosure that the objectives stated above are advantageously achieved by the present invention.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A prosthetic component implantable into a hollow interior portion of a first bone, said prosthetic component comprising:
    elongate stem means having a distal section and an opposing proximal section including a circumferential proximal end, said stem means further including a long axis; and
    support plate means having first and second opposing sides, said first side being disposed upon the circumferential proximal end of the stem means and including at least one flared plate surface having a medial section and flaring outwardly from said proximal end in a distal to proximal direction such that at least a portion of said medial section forms an angle with the long axis of the stem means which is greater than ninety degrees.

2. A prosthetic component as defined in claim 1, wherein said flared plate surface is flared at a greater degree of flare than the flared stem surface so as to form an angle with said stem surface of less than 180 degrees, such that said flared stem surface and said flared plate section form a unitary double-flared contact surface.

3. A prosthetic component as defined in claim 2, wherein the first side of the support plate forms a transition section with the proximal end of the stem means which is rounded so as to be characterized by an absence of corners and points to thereby enhance the settling action of the prosthetic component into the hollow portion of the first bone.

4. A prosthetic component as defined in claim 2, wherein substantially the entire proximal section of the stem means comprises the flared stem section and wherein the first side of the support plate means comprises the flared plate section.

5. A prosthetic component as defined in claim 4, wherein the flared stem section defines a substantially conical stem surface and the flared plate section defines a substantially conical plate surface such that the unitary double-flared contact surface comprises a unitary double-cone contact surface.

6. A prosthetic component as defined in claim 2, wherein the flared plate section forms an angle with a long axis of the stem means which is greater than ninety degrees to thereby enhance settling action of said flared plate section against the load-bearing surface of the first bone.

7. A prosthetic component as defined in claim 1, wherein the medial section of the flared plate surface extends outwardly from the proximal end of the stem means to define an overhang relative to said proximal end, said overhang being greater than any overhang which might extend outwardly from a lateral portion of said proximal end.

8. A prosthetic component as defined in claim 1, wherein the medial section of the flared plate surface forms an angle with the long axis of the stem means within a range between ninety degrees and one hundred twenty degrees.

9. A prosthetic component as defined in claim 8, wherein the medial section of the flared plate surface forms an angle with the long axis of the stem means within a range between ninety degrees and one hundred degrees.

10. A prosthetic component for implantation into a first bone for transferring mechanical stress between the first bone and a second bone, the first one having a load-bearing portion and a hollow interior portion, said prosthetic component comprising:
    elongate stem means having a long axis and further including opposing proximal and distal sections, said proximal section including a circumferential proximal edge; and
    support plate means including an at least partially non-planer first side attached to the circumferential proximal edge of the stem means and an opposing second side, said first side extending outward from said proximal edge such that said first side defines at least one flared plate section having a medial section and flaring outwardly from said proximal edge in a distal to proximal direction such that at least a portion of said medial section forms an angle with the long axis of the stem means which is greater than ninety degrees, said second side being configured to support a means for engaging with the second bone member to thereby enable load transfer between the first bone and said second bone member.

11. A prosthetic component as defined in claim 10, wherein the proximal section includes at least one flared stem section flaring outwardly in a distal to proximal direction and wherein the flared plate section is flared at a greater degree of flare than the flared stem section so as to form an angle with said stem section of less than 180 degrees, wherein the first side of the support plate means forms a circumferential transition section with the proximal edge such that said flared stem section, said transition section and said flared plate section form a unitary double-flared contact surface.

12. A prosthetic component as defined in claim 11, wherein said circumferential transition section is rounded so as to be characterized by an absence of corners and points to thereby enhance the settling action of the prosthetic component into the hollow portion of the first bone.

13. A prosthetic component as defined in claim 11, wherein substantially the entire proximal section of the stem means comprises the flared stem section and wherein entire first side of the support plate means comprises the flared plate section.

14. A prosthetic component as defined in claim 13, wherein the flared stem section defines a substantially conical stem surface and the flared plate section defines a substantially conical plate surface such that the unitary double-flared contact surface comprises a unitary double-cone contact surface.

15. A prosthetic component as defined in claim 11, wherein the flared plate section forms an angle with a long axis of the stem means which is greater than ninety degrees to thereby enhance settling action of said flared plate section against the load-bearing surface of the first bone.

16. A prosthetic component as defined in claim 10, wherein the support plate means comprises medial, lateral, anterior and posterior sides, and wherein said medial, anterior and posterior sides collectively comprise said flared plate section.

17. A prosthetic component as defined in claim 10, wherein the stem means includes opposing anterior and posterior sides flaring outwardly in a distal to proximal direction and which collectively comprise a flared stem section.

18. A prosthetic component as defined in claim 10, wherein the stem means includes medial, lateral, anterior and posterior sides, said prosthetic component further comprising:

a medial triangular projection disposed upon the medial side of the stem means and projecting outward therefrom in a medial direction to increase surface area of contact of the prosthetic component with the first bone to thereby provide increased rotational stability of said prosthetic component relative to said first bone;

wherein the medial triangular projection includes a rounded medial end intercoupling opposing sides which flare outwardly from said medial end in medial to lateral directions such that a cross section of said medial triangular projection taken along a plane perpendicular to the long axis of the stem means defines a conical section having a rounded tip which corresponds to the rounded medial end.

19. A prosthetic component as defined in claim 10 wherein the stem means and support plate means collectively comprise a femoral component of a hip prosthesis configured for insertion into a femur to thereby enable load transfer between the femur and acetabulum of a hip joint.

20. A prosthetic component as defined in claim 10 wherein the flared plate section generally forms an angle within a range of approximately 25 degrees to 35 degrees with respect to the second side of the support plate means.

21. A method for replacing a joint in a patient comprising the steps of:

(a) selecting a prosthetic component including a proximal section and a flared plate section flaring outward from said proximal section and a joint motion surface extending outward from the plate section and a stem having a long axis, wherein the flared plate section includes a medial section configured such that at least a portion of said medial section forms an angle with the long axis of the stem which is greater than ninety degrees;

(b) inserting the prosthetic component into a medullary cavity of a first bone such that the proximal section engages with side walls of the medullary cavity in tandem with the flared plate section engaging with a load-bearing portion of the first bone; and (c) inserting the joint motion surface into a second bone member to thereby enable load transfer between the first bone and the second bone member.

22. A method as defined in claim 21, further comprising the step of:

(d) preparing the load-bearing surface of the first bone and placing the flared plate section into contact therewith such that contacting portions of said flared plate section with the load-bearing surface form an angle with a long axis of the medullary cavity which is greater than ninety degrees to thereby enhance settling action of said flared plate section against said load-bearing surface.

23. A method as defined in claim 22, wherein step (b) further comprises inserting the prosthetic component into a femoral canal, and wherein step (c) further comprises inserting the joint motion surface into a corresponding acetabulum.

* * * * *